US006596862B2

(12) United States Patent
Böttcher et al.

(10) Patent No.: US 6,596,862 B2
(45) Date of Patent: Jul. 22, 2003

(54) PURIFICATION OF N-VINYL-ε-CAPROLACTAM

(75) Inventors: Arnd Böttcher, Frankenthal (DE); Rolf Pinkos, Bad Dürkheim (DE); Rudolf Erich Lorenz, Ludwigshafen (DE); Heike Becker, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 6 days.

(21) Appl. No.: 10/152,637

(22) Filed: May 23, 2002

(65) Prior Publication Data
US 2003/0004284 A1 Jan. 2, 2003

(30) Foreign Application Priority Data
May 30, 2001 (DE) .......................... 101 26 362

(51) Int. Cl.$^7$ .......................... C07D 223/10
(52) U.S. Cl. .......................... 540/540
(58) Field of Search .......................... 540/540

(56) References Cited

U.S. PATENT DOCUMENTS

| | | | |
|---|---|---|---|
| 2,317,804 A | 4/1943 | Reppe et al. | 266/313 |
| 2,891,058 A | 6/1959 | Walles et al. | 260/239 |
| 5,243,093 A | 9/1993 | Kissinger et al. | 568/724 |
| 5,329,021 A | 7/1994 | Cohen et al. | 548/543 |
| 6,384,216 B1 * | 5/2002 | Lorenz et al. | 540/540 |

FOREIGN PATENT DOCUMENTS

| GB | 1 229 022 | 4/1971 |
|---|---|---|
| GB | 1 572 423 | 7/1980 |

OTHER PUBLICATIONS

Reppe et al. "Aus dem Hauptlaboratorium der Badische Anilin–und Soda–Fabrik AG" Liebigs Ann. Chem. vol. 601 (1956) pp. 81–137.

* cited by examiner

*Primary Examiner*—Bruck Kifle
(74) *Attorney, Agent, or Firm*—Keil & Weinkauf

(57) ABSTRACT

A process for purifying N-vinyl-ε-caprolactam comprises converting the N-vinyl-ε-caprolactam which is to be purified and has a purity of at least 95% by weight into a melt, partially crystallizing the melt and separating the crystals from the mother liquor.

10 Claims, No Drawings

PURIFICATION OF N-VINYL-ε-CAPROLACTAM

The present invention relates to a process for purifying N-vinyl-ε-caprolactum.

N-Vinyl-ε-caprolactam is prepared on an industrial scale by vinylation of ε-caprolactam by means of acetylene under superatmospheric pressure in the presence of basic catalysts such as hydroxides and alkoxides (cf., for example, U.S. Pat. No. 2,327,804 and W. Reppe et al., Liebigs Ann. Chem. 601, 1956, pp. 81-137). Other preparative methods are the elimination of alcohols from N-(α-alkoxyalkyl)caprolactams and the transvinylation of ε-caprolactam with vinyl ethers (U.S. Pat. No. 2,891,058). The isolation of the N-vinylcaprolactam from the reaction mixture customarily comprises a single or multiple distillation of the crude product obtained in the reaction. The product obtained after distillation generally contains from 98 to 99.95% of the desired product, with the main impurity being ε-caprolactam. The N-vinyl-ε-caprolactam which has been prepared in this way generally has a color number in the range from 20 to 200 (APHA color numbers in accordance with DIN EN 1557). On storage, further discoloration tends to occur, i.e. the color number increases. Such discoloration occurs particularly when the N-vinyl-ε-caprolactam, which is customarily stored as a solid, is melted.

Homopolymers and copolymers of N-vinyl-ε-caprolactam are employed in many fields. N-Vinyl-ε-caprolactam is frequently used for preparing polymers for cosmetic products, for the pharmaceutical sector and for food technology. In addition, N-vinyl-ε-caprolactam and its polymers are used for coating optical fibers. In all these fields, the purity of the N-vinyl-ε-caprolactam has to meet strict requirements. Particularly for the last-mentioned application, the abovementioned discoloration of the N-vinyl-ε-caprolactam is problematical. An important quality criterion for the N-vinyl-ε-caprolactam is therefore low discoloration. The degree of discoloration is customarily measured by means of the APHA color number which is determined by a method such as that described in DIN EN 1557.

U.S. Pat. No. 2,891,058 reports the analytical crystallization of N-vinyl-ε-caprolactam from diethyl ether. The product has a purity of 95%.

It is an object of the present invention to provide a process for purifying N-vinyl-ε-caprolactam which gives an N-vinyl-ε-caprolactam which displays little if any susceptibility to discoloration, i.e. has a higher color number stability than does customary N-vinyl-ε-caprolactam obtained by distillation.

We have found that this object is achieved by converting an N-vinyl-ε-caprolactam-containing product which consists predominantly, generally at least 95% by weight, of N-vinyl-ε-caprolactam into a melt, partially crystallizing this and separating the crystals from the mother liquor in which the impurities are present to give the purified N-vinyl-ε-caprolactam.

The present invention accordingly provides a process for purifying N-vinyl-ε-caprolactam, in which an N-vinyl-ε-caprolactam having a purity of at least 95% by weight is converted into a melt, this melt is partially crystallized and the crystals are separated from the mother liquor. The crystallized material obtained in this way is an N-vinylcaprolactam having a low tendency to discoloration and thus an increased color number stability compared to the at least 95% by weight pure N-vinylcaprolactam used in the form of the melt. The invention accordingly provides, in particular, a method of removing color-imparting impurities from N-vinyl-ε-caprolactam and of reducing the tendency to discoloration or improving the color number stability of N-vinyl-ε-caprolactam.

In the process of the present invention, the pure N-vinyl-ε-caprolactam is obtained from the crystals crystallized from the N-vinyl-ε-caprolactam-containing melt. Crystallization of the N-vinyl-ε-caprolactam gives a crystalline phase depleted in impurities and a liquid phase which has a higher content of impurities (mother liquor).

The crude N-vinylcaprolactam product used for the purification preferably contains at least 95% by weight and up to 99.95% by weight, in particular from 96% by weight to 99.95% by weight and particularly preferably from 97 to 99.95% by weight, of N-vinyl-ε-caprolactam.

The crystallization of the melt is usually carried out to a degree of crystallization of at least 5% and up to 95%, preferably to a degree of crystallization in the range from 10 to 90%, in particular in the range from 20 to 80% and particularly preferably in the range from 25 to 75%. The degree of crystallization referred to here is the proportion by weight of the crystals, based on the N-vinyl-ε-caprolactam present in the melt.

In a preferred embodiment of the invention, use is made of an N-vinylcaprolactam which has been obtained by purification by distillation of an N-vinyl-ε-caprolactam-containing crude product from the production process, preferably the above-mentioned vinylation of ε-caprolactam with acetylene. For the purposes of the present invention, "purification by distillation of the crude product" means that the reaction product obtained in the production process is worked up in a customary manner and the crude product obtained in this way is subjected to at least one distillation step, preferably a fractional distillation. The distillation is preferably carried out under reduced pressure, in particular from 5 to 200 mbar corresponding to a temperature at the top in the range from 100 to 150° C.

The upper limit to the temperature at which the crystallization is carried out is naturally the temperature at which the N-vinyl-ε-caprolactam which has already crystallized is in equilibrium with the N-vinyl-ε-caprolactam present in the mother liquor (equilibrium temperature). This temperature can, depending on the type and amount of impurities, be in the range from 32 to +34.9° C. and can be determined by a person skilled in the art using customary methods. Of course, the melt can also be crystallized by cooling to temperatures below the equilibrium temperature, e.g. to temperatures which are up to 35 K and preferably from 0.1 K to 20 K below the equilibrium temperature of the melt. However, highly super-cooled melts are preferably avoided, so that the temperature employed for the crystallization of the melt is in particular no more than 10 K and particularly preferably no more than 5 K below the equilibrium temperature. The crystallization is therefore preferably carried out at temperatures of the melt to be purified in the range from 25 to 34.9° C., in particular in the range from 30 to 34.9° C.

The actual crystallization of the N-vinyl-ε-caprolactam-containing melt can be carried out by methods analogous to known crystallization processes of the prior art. Suitable crystallization processes are known from, for example, U.S. Pat. No. 5,329,021, DE-A 26 06 364, DE-A 17 69 123 and EP-A 475 893.

To carry out the crystallization, it is usual to introduce the crude product to be purified in the form of its melt into a crystallizer and to crystallize out part of the N-vinyl-ε-caprolactam by cooling the crude product. The N-vinyl-ε-caprolactam-containing mother liquor obtained is separated off.

The crystallizer used in the process of the present invention is subjected to no particular restriction. Crystallizers which have been found to be particularly useful are ones whose function is based on the formation of crystals on cooled surfaces. Such crystallization processes are also referred to as layer crystallization. Suitable apparatuses are described in DE-A 17 69 123, DE-A 26 06 364, EP-A 218 545, EP-A 323 377, CH 645278, FR 2668946 and U.S. Pat. No. 3,597,164.

To carry out layer crystallization, the N-vinyl-ε-caprolactam-containing melt is brought into contact with the cooled surfaces of the heat exchanger. The temperature of these heat exchanger surfaces can be up to 40 K below the abovementioned equilibrium temperature and is preferably from 35 to 10 K, in particular from 25 to 15 K, below the equilibrium temperature of the melt to be purified.

It has been found to be useful in the crystallization for the temperature of the cooled heat-exchange surfaces of the crystallizer which are in contact with the melt to be reduced as the crystallization progresses.

When the desired degree of crystallization has been reached, cooling is stopped and the liquid mother liquor is discharged, e.g. by pumping out or allowing it to flow out. The purified, crystallized N-vinyl-ε-caprolactam is generally isolated by heating the heat exchanger surfaces to a temperature above the melting point of the N-vinyl-ε-caprolactam, so that the purified N-vinyl-ε-caprolactam is obtained as a melt and is isolated as such. If appropriate, further purification steps are carried out before isolation of the purified N-vinyl-ε-caprolactam.

As an additional purification step, it is possible, for example, to carry out sweating of the crystal layer deposited on the heat exchanger surfaces. Here, the temperature of the crystal layer is increased a little so that the more highly contaminated regions of the crystal layer preferentially melt and flow away, thus achieving additional purification. The product which has been sweated off is then added to the mother liquor and processed further together with the latter. The crystal layer can also be treated with a cleaning liquid, for example a melt of purified N-vinyl-ε-caprolactam.

It has been found to be advantageous for the layer crystallization to be carried out in the presence of seed crystals. The use of seed crystals is known from, for example, EP-A 767 169. In such a method, the surfaces of the crystallizer from which crystals grow during the crystallization are preferably coated with a nucleating layer of N-vinylcaprolactam prior to the crystallization. The seed crystals can be obtained either from the crude product to be purified or from a melt of purified N-vinyl-ε-caprolactam. For example, seed crystals can be produced on the surfaces of the crystallizer on which crystal growth is to take place by producing an N-vinyl-ε-caprolactam-containing melt film on these surfaces and freezing this on, for example by cooling to a temperature below the melting point. The seed crystals are preferably produced by applying a film of a suspension of N-vinyl-ε-caprolactam crystals in an N-vinyl-ε-caprolactam melt and subsequently freezing this film on. The freezing-on is preferably carried out at a temperature in the region of the equilibrium temperature.

Such a suspension can be produced by freezing out a small amount of crystals from the crude product or from a melt of the purified N-vinyl-ε-caprolactam by supercooling. For example, crystals can be frozen out from an N-vinyl-ε-caprolactam-containing melt (crude product or melt of purified N-vinyl-ε-caprolactam) by indirect cooling in scratch coolers or stirred vessels with stirrers going around the wall and suspending these crystals in the melt with the aid of scraper elements on the cooled walls. The seed crystals can also be produced directly in the melt by cooling the melt to a temperature below the melting point either by means of the crystallizer or by means of cooling elements (for example cooling fingers or cooling sections) installed in the crystallizer. The seed crystals are preferably produced in an amount of from 0.1 to 700 g/kg of melt, in particular in the range from 1 to 300 g/kg of melt.

In a preferred embodiment of layer crystallization, the suspension is applied to the crystallizer surfaces by filling the crystallizer with the suspension and subsequently emptying it. After it has been emptied, a layer of suspension remains on the crystallizer surfaces and this is then frozen on, preferably in the region of its equilibrium temperature.

The crystallization on cooling surfaces can be carried out as a dynamic or static process. Preference is given to using dynamic processes. Static processes are described, for example, in U.S. Pat. No. 3,597,164, EP 323 377 and FR 2668946, which are hereby incorporated by reference. In the static processes, mass transfer in the liquid phase takes place only by means of free convection (melt at rest).

In the case of the dynamic crystallization processes, the crude product to be crystallized is kept in motion. This can be carried out by forced flow in heat exchangers which are filled with the flowing medium, for example as described in DE 26 06 364, or by passing a trickling film over a cooled wall, for example as described in DE-B 1 769 123 and EP-A 218 545, or by means of moving cooling surfaces such as cooling rolls or cooling belts. Dynamic layer crystallization is preferably carried out in heat exchangers filled with flowing medium, for example in externally cooled tubes or bundles of tubes.

In dynamic layer crystallization processes, in particular those which are carried out in heat exchangers filled with flowing medium, the procedure is generally to apply any desired seed crystal layer to the heat exchanger surfaces of the crystallizer and then to bring the N-vinyl-ε-caprolactam-containing crude product into contact with the cooled heat exchanger surfaces, for example by allowing the melt to be purified to flow through the cooled tubes of the crystallizer. This results in partial crystallization of the N-vinyl-ε-caprolactam from the crude product. In general, this procedure is stopped when the amount of N-vinyl-ε-caprolactam which has crystallized out just still allows sufficient flow of the melt through the heat exchanger. For this purpose, the liquid phase (mother liquor) is removed and the crystallized N-vinyl-ε-caprolactam is then isolated in the above-described manner by, if appropriate after a further purification step, heating the heat exchanger surfaces to a temperature above the melting point of N-vinyl-ε-caprolactam. This procedure can be repeated a number of times until the desired amount of N-vinyl-ε-caprolactam has been crystallized from the crude product.

As an alternative to layer crystallization, the crystallization can also be carried out as a suspension crystallization. In suspension crystallization, individual crystals are formed in the body of the N-vinyl-ε-caprolactam-containing, liquid crude product by removal of heat. The crystal suspension obtained in this way is kept in motion during the suspension crystallization process, for which pumped circulation or stirring is particularly useful. Adhesion of crystals to heat exchanger surfaces is not necessary and is in fact undesirable. Suspension crystallization is naturally classified as a dynamic crystallization process since the crude product is kept in motion during crystallization. As regards the temperatures of the crude product required for crystallization of the N-vinyl-ε-caprolactam, what has been said above applies.

In suspension crystallization, the heat is generally removed by indirect cooling, for example via scratch coolers which are connected to a stirred vessel or a vessel without an agitator. Circulation of the crystal suspension is in this case achieved by means of a pump. It is also possible to remove the heat via walls of the stirred vessel having stirrers going around the wall. Cooling disc crystallizers, as manufactured by, for example, GMF (Gouda in The Netherlands), can also be used for heat removal. Of course, the heat can also be removed by cooling by means of conventional heat exchangers (preferably shell-and-tube or plate heat exchangers). However, the procedures here are different from the above-mentioned measures for removing heat to form crystal layers on the heat transfer surfaces. If, during operation, a state in which the heat transfer resistance reaches an excessively high value due to encrustations is reached, a switch is made to a second heat exchanger. During the operating period of the second heat exchanger, the first heat exchanger is then regenerated, for example by melting off the crystal layer. When an excessively high heat transfer resistance has been reached in the second heat exchanger, a switch is made back to the first heat exchanger. This procedure can also be carried out using more than two heat exchangers alternately. The heat can also be removed by conventional partial evaporation of the crude product under reduced pressure.

The separation of the N-vinyl-ε-caprolactam-enriched crystals obtained in the suspension crystallization from the depleted mother liquor is carried out by the known methods of solid/liquid separation, for example by filtration, sedimentation and/or centrifugation. In the case of a crystallized material at rest, the mother liquor can also be removed by allowing it to run off. In the case of filtration, sedimentation or centrifugation, a prethickening of the suspension is preferably carried out, for example by means of hydrocyclones. Centrifugation can be carried out using all known centrifuges which operate discontinuously or continuously. It is particularly advantageous to use pusher centrifuges, for which single-stage or multistage operation is possible. Also suitable are screw screen centrifuges or screw discharge centrifuges (decanters). Filtration is generally carried out by means of suction filters which are operated continuously or batchwise, with or without an agitator, or by means of belt filters. Filtration can also be carried out under pressure or under reduced pressure.

Further process steps for increasing the purity of the crystals or the crystal cake can be provided during and/or after the solid/liquid separation. After separating the crystals from the mother liquor, preference is given to carrying out single-stage or multistage washing and/or sweating of the crystals or the crystal cake. As washing liquid, preference is given to using liquid N-vinyl-ε-caprolactam whose purity is greater than that of the mother liquor. Washing can be carried out in apparatuses customary for this purpose, for example in centrifuges or in suction filters or belt filters. Washing can be carried out in one or more stages, with the washing liquid preferably being conveyed in countercurrent to the crystal cake. In the case of a multistage crystallization, it is particularly advantageous to use the feed to a crystallization stage as washing liquid for the crystals from this same crystallization stage. The mass ratio of washing liquid to crystals is preferably in the range from 0.1 to 1 kg, particularly preferably in the range from 0.2 to 0.6 kg, of washing liquid per kg of crystals.

The crystals obtained in a suspension crystallization are particularly preferably purified by carrying out the above-described washing procedure, in particular on centrifuges or belt filters. Of course, it is also possible for combined washing and sweating procedures to be carried out in one apparatus.

The purification of the crystals obtained in suspension crystallization is preferably carried out using washing columns in which the crystals, generally after prethickening, e.g. by filtration or sedimentation, are conveyed in countercurrent to a washing liquid, either continuously or batchwise. As washing liquid, preference is given to using a melt of the previously purified crystals. Transport of the crystals in a direction opposite to the direction of flow of the liquid can be achieved in a customary manner, e.g. by means of gravity, preferably by means of mechanical transport or by means of hydraulic forces (e.g. pressure drops occurring during flow through the mass of crystals).

All the abovementioned crystallization processes can be operated continuously or batchwise.

The preferred dynamic layer crystallization is preferably carried out batchwise, particularly when it is carried out in heat exchangers filled with flowing medium, as described above. However, integration into a continuous purification process is readily possible, for example with the aid of vessels for intermediate storage of the melt or the mother liquor.

The purified N-vinyl-ε-caprolactam obtained in the first crystallization stage can, if desired, be subjected to further crystallization steps. Likewise, the mother liquor can be crystallized once again in the above-described manner to obtain further N-vinyl-ε-caprolactam. The crystallization is frequently also carried out as a multistage process in which an N-vinyl-ε-caprolactam-containing melt is firstly crystallized to a desired degree of crystallization and separated into crystals and mother liquor ($1^{st}$ crystallization stage). The mother liquor is then subjected to a further crystallization and once again separated into mother liquor and crystals ($-1^{st}$ crystallization stage). This procedure can be repeated one or more times using the mother liquor from the $-1^{st}$ stage ($-2^{nd}$ crystallization stage, etc.). The crystals from the $-1^{st}$ crystallization are preferably combined with the melt to be purified, while the crystals from the $-2^{nd}$ stage are combined with the mother liquor from the $-1^{st}$ stage, etc. Likewise, the primary crystals from the $1^{st}$ crystallization stage can be passed to one or more further crystallization stages ($2^{nd}$, $3^{rd}$ or $4^{th}$ crystallization stage, etc.), with the mother liquor from the $2^{nd}$ crystallization stage preferably being combined with the melt to be purified and a corresponding procedure being employed in the higher crystallization stages.

The purified N-vinyl-ε-caprolactam obtained in the crystallization has a very low tendency to suffer discoloration and thus an improved color number stability. In general, it contains less than 0.9% by weight, in particular less than 0.1% by weight and particularly preferably less than 0.05% by weight, of impurities. The N-vinyl-ε-caprolactam obtained in this way meets the requirements of the food industry, of the cosmetics and pharmaceutical sectors and of the optical fibers sector.

In the case of crystallization of N-vinyl-ε-caprolactam which contains stabilizers (polymerization inhibitors) customary for this purpose, it has surprisingly been found that an amount of stabilizer sufficient for stabilizing the N-vinyl-ε-caprolactam remains in the crystallized material. Unlike the case of the customary distillation processes in which these stabilizers are quantitatively removed, crystallized N-vinylcaprolactam does not have to be restabilized, which results in a reduction in the risk of spontaneous polymerization of the purified N-vinylcaprolactam.

The stabilizers are usually used in an amount of from 5 to 100 ppm, in particular from 10 to 30 ppm (by weight, based on N-vinylcaprolactam).

The stabilizers for N-vinyl-ε-caprolactam are generally compounds of the formula I

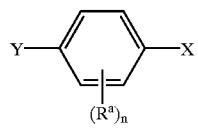

where the variables X and Y are each, independently of one another, an OH, OR, NHR or NRR' group, where R and R' are each, independently of one another, $C_1$-$C_8$-alkyl, n is 0, 1 or 2 and $R^a$ is $C_1$-$C_4$-alkyl.

Here, $C_1$-$C_8$-alkyl is a straight-chain or branched alkyl group having from 1 to 8 carbon atoms, preferably from 1 to 4 carbon atoms, e.g. methyl, ethyl, n-propyl, 2-propyl, 1-butyl, 2-butyl, isobutyl, tert-Butyl, n-pentyl, 2- or 3-pentyl, isopentyl, neopentyl, 3-methylbut-1-yl, 3-methybutan-2-yl, 2-methylbut-2-yl, n-hexyl, 2- or 3-hexyl, 2-methylpent-1-yl, n-heptyl, 2-, 3- or 4-heptyl, 2-methylhex-1-yl, n-octyl, 1-methylhept-1-yl, 2-ethylhex-1-yl. Among the compounds of the formula I, preference is given to those compounds in which X and Y are an NHR group, and to compounds in which X is OH or OR and Y is OR. n is preferably 0. If n is different from 0, $R^a$ is preferably methyl.

The following examples serve to illustrate the process of the present invention and do not imply any restriction.

All purities reported in % are gas-chromatographic purities and correspond to the ratios of the peak areas.

EXAMPLE 1

Crystallization of a Nonstabilized Sample of N-vinyl-ε-Caprolactam

N-Vinyl-ε-caprolactam having a purity of 99.8% and an ε-caprolactam content of 0.15%, a melting point of 34.5° C. and a color number of 32 APHA was split at about 40° C. into a test sample (200 ml) and a blank (100 ml). The test sample was crystallized in a vesel at an ambient temperature of 25° C. After about 60% by weight had crystallized out, the mother liquor was poured off. Blank, crystals and mother liquor were melted individually at 50° C. and the color number was determined. The color numbers are reported in table 1. All samples were subsequently stored at 25° C. for 2 days, then melted again at 50° C. and the color number was redetermined. The color numbers are reported in table 1.

TABLE 1

| Sample | Color number APHA immediate | Color number APHA after 2 d |
|---|---|---|
| Blank | 51 | 86 |
| Crystals | 35 | 63 |
| Mother liquor | 63 | 102 |

EXAMPLE 2

Crystallization of a Stabilized Sample of N-Vinyl-ε-Caprolactam

N-Vinyl-ε-caprolactam having a purity of 99.8%, an ε-caprolactam content of 0.15%, a melting point of 34.5° C. and a color number of 40 APHA and containing 10 ppm of 1,4-(2-butylamino)benzene was split as described in example 1 into a test sample and a blank. The crystallization of the test sample and the determination of the color numbers were carried out as in example 1. The color numbers determined are reported in table 2. The crystallized material still contained 5 ppm of stabilizer.

TABLE 1

| Sample | Color number APHA immediate | Color number APHA after 2 d |
|---|---|---|
| Blank | 60 | 90 |
| Crystals | 36 | 66 |
| Mother liquor | 75 | 115 |

We claim:

1. A process for purifying N-vinyl-ε-caprolactam, which comprises converting the N-vinyl-ε-caprolactam which is to be purified and has a purity of at least 95% by weight into a melt, partially crystallizing the melt and separating the crystals from the mother liquor.

2. A process as claimed in claim 1, wherein the crystallization is carried out to a degree of crystallization in the range from 10 to 90%.

3. A process as claimed in claim 1, wherein the crystallization is carried out at a melt temperature in the range from 25 to +34.9° C.

4. A process as claimed in claim 1, wherein the crystallization is carried out in the presence of seed crystals of N-vinyl-ε-caprolactam.

5. A process as claimed in claim 1, wherein the crystallization is carried out on cooled surfaces.

6. A process as claimed in claim 1, wherein the crystallization is carried out by a dynamic crystallization method.

7. A process as claimed in claim 1, wherein the N-vinyl-ε-caprolactam used has been obtained by purification by distillation of an N-vinyl-ε-caprolactam-containing crude product from the production process.

8. A process as claimed in claim 7, wherein the purity of the N-vinyl-ε-caprolactam to be purified is from 98 to 99.95% by weight.

9. A process as claimed in claim 1, wherein the melt contains at least one polymerization inhibitor in an amount of from 5 to 100 ppm by weight.

10. A process as claimed in claim 9, wherein the polymerization inhibitor is selected from among the compounds of the formula I

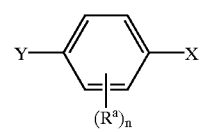

where, in formula I, the variables X and Y are each, independently of one another, an OH, OR, NHR or NRR' group, where R and R' are each, independently of one another, $C_1$–$C_6$-alkyl, n is 0, 1 or 2 and $R^a$ is $C_1$–$C_4$-alkyl.

* * * * *